United States Patent [19]
Sutter

[11] Patent Number: 6,086,206
[45] Date of Patent: Jul. 11, 2000

[54] ANALYSIS METHOD FOR ENHANCING AND EXTRACTING SECOND ORDER NONLINEAR RESPONSE COMPONENTS OF THE MULTI-AREA ELECTRORETINOGRAM

[76] Inventor: Erich E. Sutter, 711 Palomar Dr., Redwood City, Calif. 94062

[21] Appl. No.: 09/003,060

[22] Filed: Jan. 5, 1998

[51] Int. Cl.$^7$ ........................................................ A61B 3/00
[52] U.S. Cl. ................................................................ 351/224
[58] Field of Search .................................... 351/209, 210, 351/211, 222, 224, 246; 600/558, 27

[56] References Cited

U.S. PATENT DOCUMENTS

| | | | |
|---|---|---|---|
| 4,846,567 | 7/1989 | Sutter | 351/224 |
| 4,889,422 | 12/1989 | Pavlidis | 351/210 |
| 5,149,317 | 9/1992 | Robinson | 600/27 |

*Primary Examiner*—George Manuel
*Attorney, Agent, or Firm*—David Pressman

[57] ABSTRACT

Two new modes of stimulation and analysis are provided for the enhancement of local and lateral nonlinear interactions in the multi-area electroretinogram. In both modes the stimulation consists of a sequence of stimulus intervals (40) of equal size. In mode 1 each stimulus interval may contain two stimuli of the same or different type. Stimulus 1 occurs at a predetermined time within each interval (40) while stimulus occurs pseudorandomly at the beginning of the intervals. The same pseudorandom stimulation is used for all stimulated areas (12) with and appropriate shift in the stimulus sequence from one area to the next. Multi-area responses are derived by cross-correlating the response cycle with a sequence of the same length with values of +1 and −1 at the beginning of each stimulus interval to reflect the pseudorandom stimulation and 0 everywhere else. In mode 2 each stimulus interval contains pseudorandom stimuli at different time points (50) within each stimulus interval. The stimuli at different time points are controlled by the same pseudorandom sequence with an appropriate shift in the sequence from one time point to the next. Stimuli at different time points may be of the same or of different type. A stimulus of the same or different type can be presented at the beginning of each stimulus interval (40). Multi-area responses are derived by cross-correlating the response cycle with a sequence of the same length with +1 and −1 at the time point 1 of each stimulus interval reflecting the pseudorandom stimulation at this time point and 0 everywhere else. Mode 2 yields the responses generated by the stimuli at each time point in the stimulus interval for each stimulated area.

9 Claims, 9 Drawing Sheets

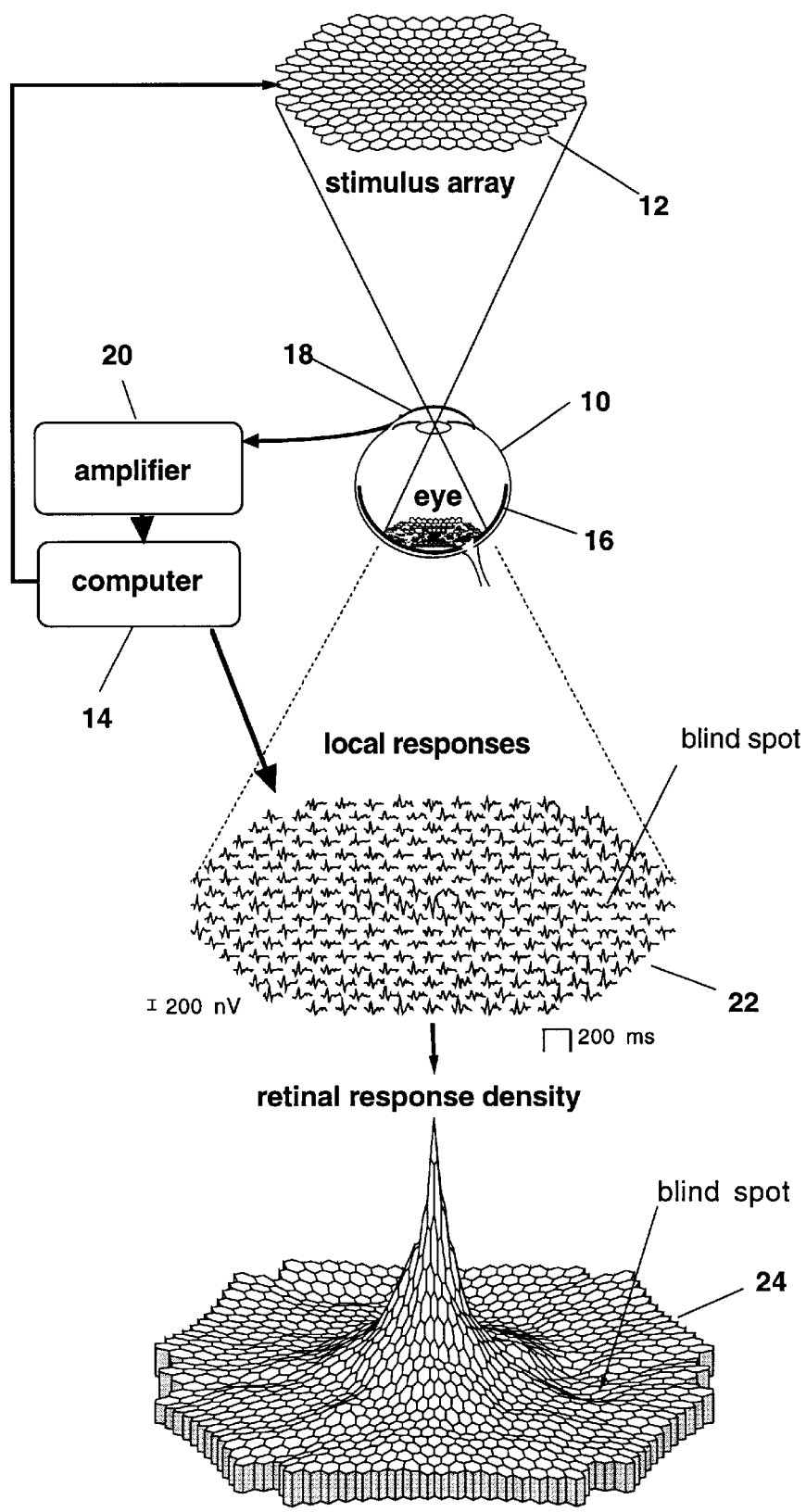
Fig. 1 --- Prior Art

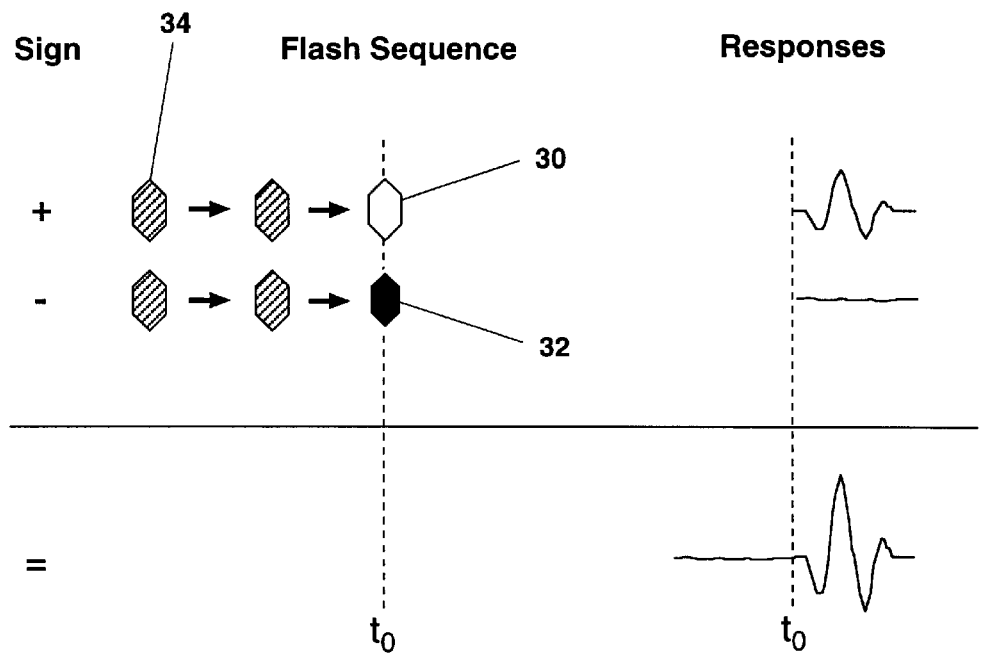
Figure 2a -- Prior Art
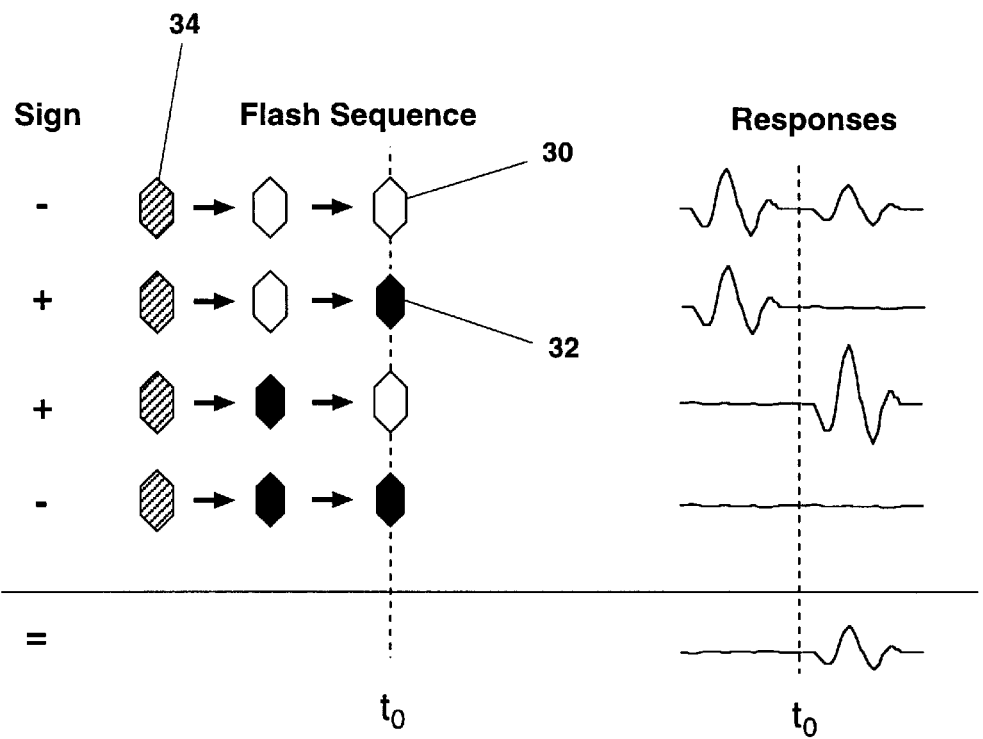
Figure 2b -- Prior Art

Data Collection
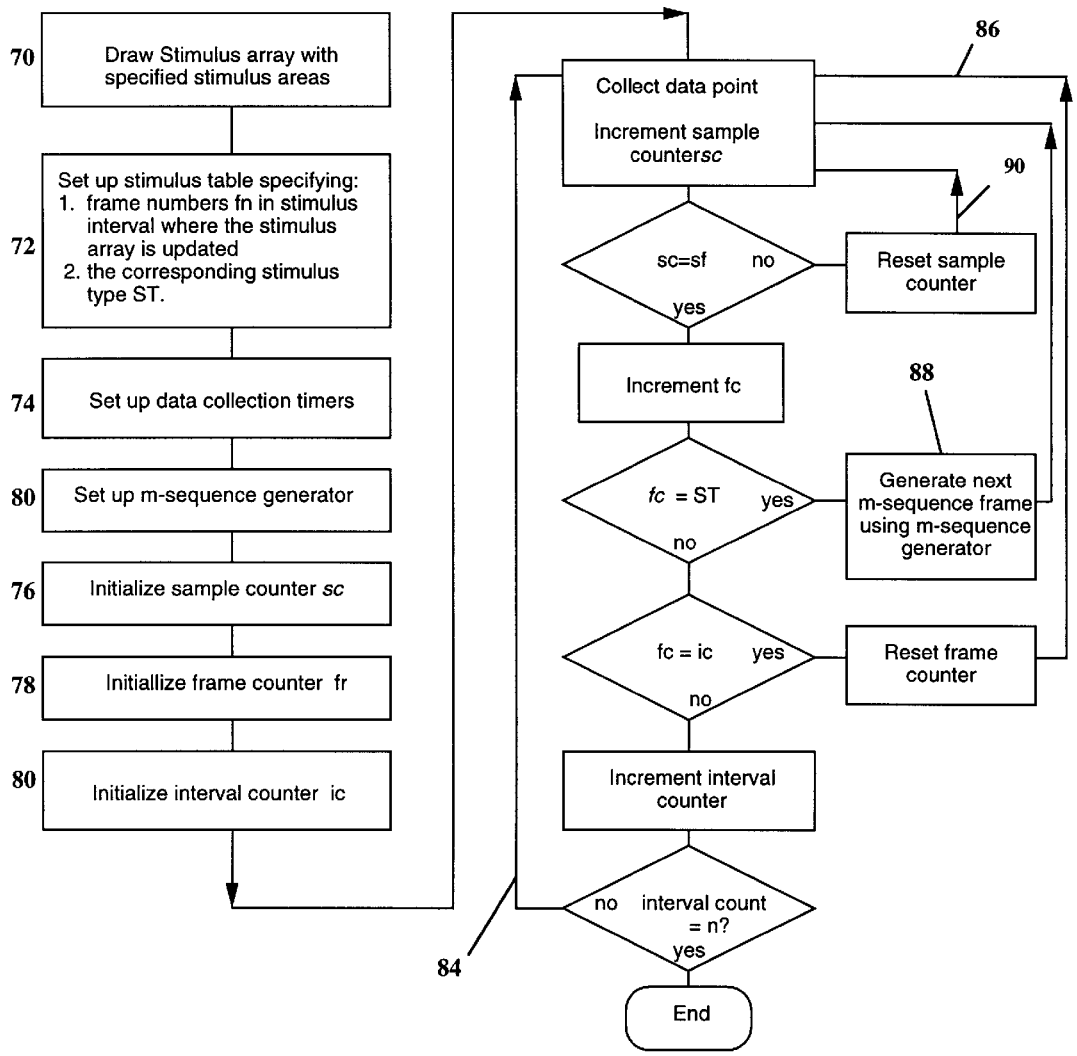
Data Processing
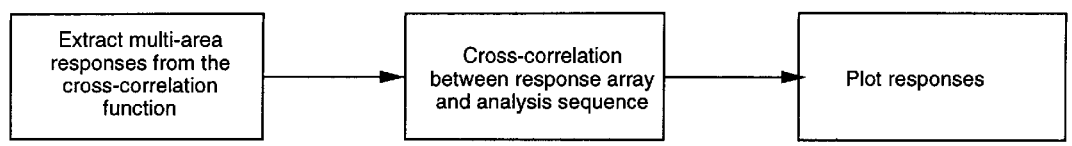
Figure 9

ANALYSIS METHOD FOR ENHANCING AND EXTRACTING SECOND ORDER NONLINEAR RESPONSE COMPONENTS OF THE MULTI-AREA ELECTRORETINOGRAM

GOVERNMENT CONTRACT

The U.S. government has rights in the claimed invention pursuant to NIH Grant EY-6861.

BACKGROUND—CROSS-REFERENCE TO RELATED APPLICATION

The invention of this patent is an modification of the system of my earlier U.S. Pat. No. 4,846,567 titled "Retinal Area Response Mapping Using Simultaneous Multi-Area Stimulation with Binary M-sequences and Objective Response Mapping", granted Jul. 11, 1989.

BACKGROUND—FIELD OF INVENTION

This invention relates to the testing of visual function, specifically to such testing by a modification of the pseudorandom stimulation technique described my above patent. The invention enhances and isolates response components due to adaptive mechanisms. These components of the bio-electrical response from the retina are of particular importance for the diagnosis and management of diseases affecting the retina and the optic nerve. The invention permits simultaneous derivation of these components from a large number of retinal areas for the generation of topographic maps of retinal function.

BACKGROUND—DESCRIPTION OF PRIOR ART—FIGS. 1 AND 2

The Multi-input M-sequence Technique Applied to Visual Evoked Responses

Early detection of retinal disease and objective evaluation of treatment require noninvasive testing of retinal function. As retinal dysfunctions commonly begin in small patches, such testing is most effective when conducted locally. When a large number of retinal areas are tested, a map of the retina can be generated with the function of each area indicated in the map.

A known method of mapping of retinal function, detailed in my above patent, is schematically illustrated in FIG. 1.

A subject's eye 10 fixates on the center of an array of stimulus elements 12 on a CRT (cathode ray tube—not shown) display. These elements may be of different shapes or sizes. Typically an array of densely packed hexagons or squares is used.

All the elements are concurrently but independently and pseudorandomly switching between two states controlled by a computer 14, e.g., between black and white states. Each element thus stimulates a corresponding area on a retina 16 of the subject. This visual stimulus generates or evokes bioelectrical responses in the retinal layers.

This evoked signal can be detected on the cornea of the eye by means of a special electrode 18. Such electrodes may consist of a thin conducting fiber or gold foil placed under the lower lid or a metal ring (not shown) surrounding a contact lens (not shown) covering the cornea which is not shown, but is directly under electrode 18. The response signal is amplified by an amplifier 20.

A special method of independent temporal modulation of the multiple areas permits extraction of the local responses from the response signal. The temporal modulation follows a special type of pseudo-random binary sequences, called binary m-sequences and discussed infra. This class of sequences has special properties that render it particularly useful for the purpose. Other pseudorandom sequences can also be used, but this leads to somewhat degraded estimates for the multi-area response components as well as a more complex procedure and a higher computational load in the derivation of higher order response components. All areas are stimulated with the same sequence. However each element is given a different starting point in the sequence so that the contributions of all the elements to the compound response will be uncorrelated.

Local responses 22 are extracted by computation of the cross-correlation function between the applied m-sequence and the evoked response signal. The extraction is executed after completion of the recording by computer 14 by means of a special algorithm. From the array of local responses 22, a response density plot 24 is derived by means of computer 14.

The stimulus is pseudorandom and, therefore, cyclical. The response is recorded in overlapping segments spliced together to a seamless cycle. The cross-correlation function between the stimulus and response cycles is another cycle of the same length. For computation of the cross-correlation function it is used a sequence of +1 and −1. The first order kernel derived from this procedure is the sum of all responses following a stimulus interval with a stimulus minus the sum of all signals following a stimulus interval without a stimulus. Both types of stimulus intervals occur approximately the same number of times during the pseudorandom stimulation.

This process is schematically illustrated in FIG. 2a. The white hexagonal patches 30 represent stimulation of the patch while the black hexagons 32 represent non-stimulation. For the specific sequence of white and black hexagons shown in each row, the shaded hexagons 34 occur in both states approximately an equal number of times when a pseudorandom sequence is used for stimulation.

The basic analysis technique used in my above patent is commonly considered to belong to a class of methods called white noise analysis. In this method a system with single or multiple inputs is stimulated with pseudorandom stimuli and the response is derived by means of cross-correlations. The cross-correlations yield different terms, called binary kernels, that describe the response of the system. The first order kernel, usually the second largest term, is obtained through cross-correlation of the response cycle with the a sequence of +1 and −1 reflecting the pseudorandom stimulus. The first slice of the second order kernel is computed through cross-correlation of the response cycle with a binary cycle with a cycle obtained by multiplying neighboring elements of the stimulation cycle (again as a sequence of +1 and −1). This component describes interactions between pairs of stimuli applied to the same stimulus patch.

The binary kernels are equivalent to averages of the responses following all stimulus segments of a given length occurring during the pseudorandom stimulation using the weight factors +1 or −1. For the first order kernel the weight factor is selected according the last stimulus in each segment as shown in FIG. 2a left column. For the first slice of the second order kernel the weight factor is selected in accordance with the last two consecutive stimuli as shown in FIG. 2b. For clarity the stimulus interval is shown large enough to accommodate the entire response waveform. In practice this is not always the case and the responses generated in consecutive stimulus intervals overlap. My above invention teaches how the white noise analysis technique can be optimized for testing of systems with multiple inputs using a special class of pseudorandom sequences called binary m-sequences.

Medical Applications of the Multi-area Technique

Instruments based upon the system of above patent are currently in use in numerous medical centers and research laboratories around the world. The main purpose of these instruments is early detection of retinal pathologies and disease management. Some of the most important applications require testing of the function of inner retinal layers, particularly the ganglion cell layer, and testing of adaptive mechanisms.

The second order component of FIG. 2b is largely due to adaptive mechanisms within the retina and originate predominantly from the inner layers of the retina. It receives a significant contribution from retinal ganglion cells, the neural substrate affected by glaucoma and optic nerve disease. The small size of this component and the still smaller contribution from ganglion cells is a great handicap in their use in the clinic.

In their early stages disease processes often affect adaptive processes of the retina and its ability to rapidly recover from stress. These properties are reflected in interactions between pairs of stimuli at the same location or at different locations on the retina. The second order component of FIG. 2b reflects such interactions at the same location. It is largely due to adaptive mechanisms within the retina and originate predominant from the inner layers of the retina. It receives a significant contribution from retinal ganglion cells, the neural substrate affected by glaucoma and optic nerve disease. The small size of this component and the still smaller contribution from ganglion cells is a great handicap in their use in the clinic.

Equally important are response components from interactions between different stimulus patches. They also contain a large contribution from ganglion cells. While the interactions between any pair of patches are often negligible in size, the sum of the interactions of any one area with all the others can be quite large and is potentially important for the clinic. However, conventional application of the multi-area technique do not permit extraction and summation of all these interaction terms. Due to their small size and their large number their isolation would require records much to long to be recorded in a clinical environment.

The small size of the above response components requires long recording times for their detection and results in a lack of sensitivity and specificity when the technique is applied for the diagnosis of retinal and optic nerve diseases.

OBJECTS OF THE INVENTION

Accordingly several objects of my invention are: 1. To provide improved maps of retinal responses. 2. To map the summed local and lateral effects of retinal adaptation and recovery from stress. 3. To modify the pseudorandom stimulation and analysis technique to provide detailed information on the time course and dynamics of adaptive processes. 4. To shorten the time necessary for mapping of the function of the inner retina and specifically of ganglion cells in the clinic. 5. To increase in the sensitivity and specificity of the multi-area technique for diagnosis of retinal diseases.

Further objects and advantages are: 6. To provide a means for studying the effects of a stimulus covering a predetermined retinal area on the following multi-area responses. 7. To provide a means for studying the effect the stimulation of each area has on the response to a stimulus covering a larger retinal region, the converse of #6.

Further objects and advantages will become apparent from a consideration of the ensuing description and the accompanying drawings.

DESCRIPTION OF DRAWINGS

FIG. 1 is a schematic representation of a prior-art system for mapping of retinal functional by means of an electroretinogram.

FIG. 2a is a schematic representation of a derivation of a first order binary kernel according to prior art.

FIG. 2b is a schematic representation of the derivation of a first slice of the second order binary kernel to prior art.

FIG. 5b is a schematic representation of the derivation of the first slice of the second order binary kernel for comparison with FIG. 5a.

FIG. 9 is a simplified flow chart for the methods of the invention.

Figure 3:
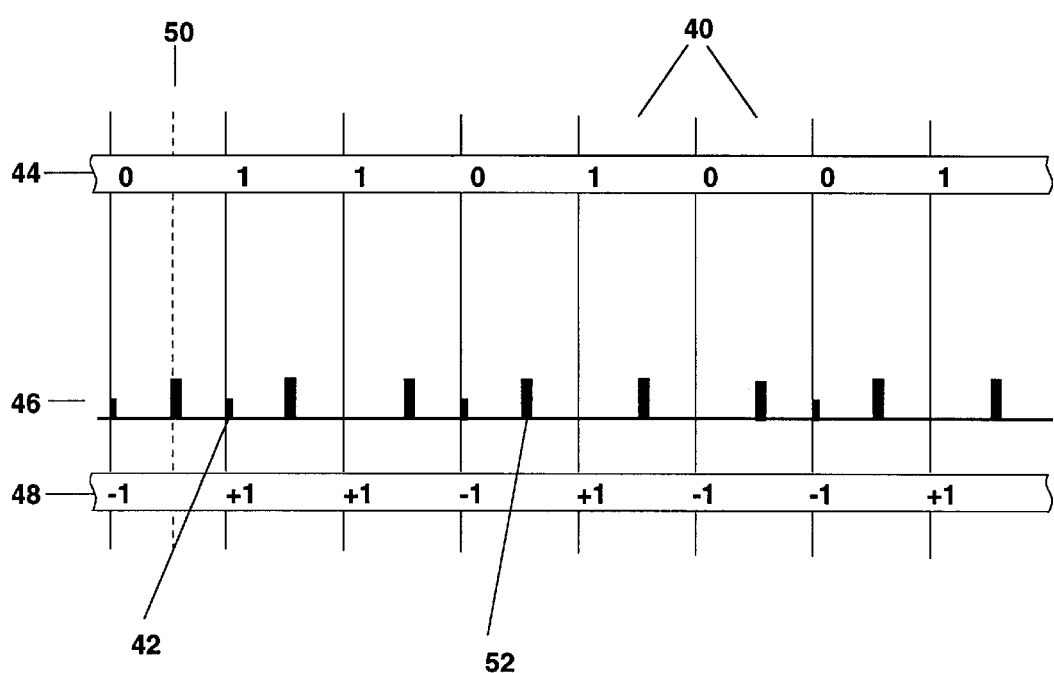
FIG. 3 is a schematic representation of stimulus and analysis sequences used to emphasize the effects of lateral mechanisms in the retina used in Mode 1 of the invention.

REFERENCE NUMERALS IN DRAWINGS 10 eye of patient
12 stimulus elements or array
14 computer
16 retina
18 corneal electrode
20 amplifier
22 array of local responses
24 response density plot
30 stimulated patch
32 non-stimulated patch
34 patch having equal probability of being stimulated or not stimulated
36 elements of an m-sequence
38 an example of a controlling sequence for mode 2
40 stimulus intervals
42 multi-area pseudorandom stimulus 44 pseudorandom sequence controlling the multi-area stimulation
46 the stimulation sequence
48 analysis sequence
50 time point in each stimulus interval of the periodic stimulus
52 periodic stimulus
60 stimulus patch 1 whose response is considered
62 stimulus patch 2 whose response is affected by stimulation of stimulus patch 1
70 routine to draws the stimulus geometry
72 routine to set up a stimulus table
74 routine to set up data collection timers
76 routine initializing a frame counter
78 routine initializing a sample counter
80 routine initializing an interval counter
82 routine to set up a table containing an m-sequence
84 stimulation cycle loop
86 stimulus interval loop
88 routine updating the stimulus
90 loop collecting a data points during each video frame
92 routine computing the cross-correlation function
94 routine extract response components
96 routine to plot data

SUMMARY

In accordance with the present invention, the multi-area technique of my above patent by a first technique to enhance effects due to interactions between stimuli in the same area and in different areas. A second modification of the technique documents the time course in the recovery of retinal responses after stress due to high intensity stimulation.

DESCRIPTION—THEORY OF THE INVENTION

The method and application of this invention utilizes the apparatus of FIG. 1 in two new modes that differ from those used in the past and produce unexpected advantages. The retinal stimulation has a special temporal structure that enhances response components of clinical importance.

In a first mode (Mode 1) stimuli controlled by elements of a pseudorandom sequence are alternated with periodic stimuli as shown in equation 1.

$$\begin{aligned} S_{2i-1} &= m_i * s_1 \\ S_{2i} &= s_2 \end{aligned} \quad \text{for } i = 1, n \tag{1}$$

Where $m_i$ are the elements of the pseudorandom sequence with values 0 and 1, n is the number of its elements and $s_1$, $s_2$ are two different types of stimuli. The stimulus sequence thus contains n stimulus intervals of equal size corresponding to the n elements of the pseudorandom sequence. Each interval contains a stimulus $s_2$. The stimulus $s_1$ is thus only present if the corresponding element of the pseudorandom sequence is a 1.

The first order response is derived by cross-correlation of the response with the sequence with values 0, +1 and −1 defined by equation 2.

$$a_{2i-1} = 2*m_i - 1$$

$$a_{2i \cdot k} = 0 \tag{2}$$

The analysis sequence must have the same number of elements as the response sequence. The response is sampled periodically at a rate faster than the rate of stimulation such that multiple data points are collected at periodic intervals between consecutive stimuli. All the elements of the analysis sequence that do not coincide with stimuli are set to zero.

FIG. 3—Stimulus Sequence and Analysis

A schematic representations of the stimulus sequence of mode 1 and the corresponding analysis sequence is shown in FIG. 3. The stimulus consists of a sequence of stimulus intervals 40 of equal length. The stimulation corresponding to a specific stimulus patch is shown in the second row 46 of FIG. 3. The first stimulus within each stimulus interval is a multi-area stimulus 42 controlled at each stimulus patch by a pseudorandom binary sequence. At a predetermined time within each stimulus interval a stimulus 52 is presented independent of the pseudorandom binary sequence. The recorded response to this stimulus sequence is cross-correlated with analysis sequence 48 shown in row 3. The analysis sequence contains a +1 at locations at all locations at the first stimulus in each stimulus interval where stimulus patch one was stimulated and a −1 where it was not stimulated. All other locations within each stimulus interval contain the value 0.

If the stimulation of multiple areas is implemented in accordance with my above patent, first order response components corresponding to stimulus patches 12 are found at periodic intervals on the cross-correlation function.

In a second mode (Mode 2) consecutive elements of a pseudorandom sequence of length n control every $k^{th}$ stimulus in the stimulus sequence where k is a predetermined number. Eight consecutive stimuli are controlled by elements of a pseudorandom sequence at intervals of n/k as defined by equation 3.

$$S_{(i \cdot k)+j} = S_j * m_{(j \cdot n/k)+i} \text{ for } j=0, \ldots, (k-1) \tag{3}$$

Accordingly the stimulus sequence consists of n stimulus intervals of the same length, each containing k stimuli $S_j$ controlled by the pseudorandom sequence. The stimuli $S_j$ within each stimulus interval can be of the same or of different type. The time intervals between the stimuli $S_j$ can be the same or different.

The first order response is derived by cross-correlation of the response with a sequence of the same length with values 0, +1 and −1 defined by equation 4.

$$a_{(i \cdot k)} = 2*m_i - 1$$

$$a_{(i \cdot k)+j} = 0 \text{ for } j \neq 0 \tag{4}$$

The response is sampled periodically and at a rate faster than the rate of stimulation such that multiple data points are collected at periodic intervals between consecutive stimuli. All the elements of the analysis sequence that do not coincide with stimuli are set to zero.

FIG. 4—Stimulus and Analysis of Modes 1 and 2 Combined

Mode 1 and mode 2 can be combined as illustrated in the stimulus sequence of equations 5 and the corresponding analysis sequence of equation 6.

$$S_{(i*k)} = s_0 \tag{5}$$
$$S_{(i*k)+j} = s_j * m_{(j*n/k)+i} \quad \text{for } j = 1, \ldots, (k-1)$$

$$a_{(i*k)+1} = 2*m_i - 1 \tag{6}$$
$$a_{i*k)+j} = 0 \text{ for } j \neq 1$$

A schematic representations showing the derivation of the stimulus and analysis sequences for a typical combination of modes 1 and 2 is shown in FIG. 4 for the case k=3. Two or more stimuli 42 are presented at the different times points 50 within the stimulus intervals 40, stimulus 1 at time point 1, stimulus 2 at time point 2, and stimulus 3 at time point 3. In consecutive stimulus intervals stimuli at the same time point within the interval are controlled each by consecutive elements in the pseudorandom sequence that controls the stimulation. The controlling sequences are shown in the bands 44. The resulting stimulus sequence is symbolically represented as a row of vertical marks 46.

From one time point to the next the controlling sequence is shifted in time by L/k steps where L is the length of the pseudorandom binary sequence and k is the number of stimulus time points in each stimulus interval. The stimuli at different time points can be of the same type or of different types. The shift in the pseudorandom stimulation from one stimulus patch to the next is L/k*i where i is the number of stimulated patches.

At a the beginning of each stimulus interval 40 a test stimulus 52 can be presented that is not controlled by the pseudorandom sequence. Its effect on the local responses is measured at time points 50 within stimulus interval 40 by means of the following pseudorandom stimuli. It is presented in every stimulus interval and its geometry is not necessarily related to the array of stimulus patches.

The recorded response to the stimulus sequence is cross-correlated with analysis sequence 48 shown in row 3. Analysis sequence 48 has a value different from 0 only at time point 1 in each stimulus interval where it contains a+1 in all if the first stimulus patch is stimulated and a−1 if it is not stimulated at this time point. The values of the analysis sequence reflect the m-sequence stimulation of stimulus patch 1 in the array of stimulus patches 12 for the first one of the time points 50 in the stimulus interval.

Interactions between the different stimuli of mode 2 are computed by cross-correlating of the response sequence with analysis sequences derived from products of the first order analysis sequences as defined by equation 7

$$a^{j_1 j_2} = a_{(i \cdot k) + j_1} \, a_{(j \cdot k) + j_2} \qquad (7)$$

Implementation of the multi-area systems analysis using a pseudorandom binary sequences that belong to the class of binary m-sequences offers numerous advantages in regard to computational effort, speed and quality of the analysis. The computational effort for the derivation of second and higher order kernels is greatly reduced. This is because binary m-sequences as sequences of −1 and +1 are identical up to a shift with all their product sequences with a relative shift different from zero. Only a single cross-correlation function between the response and the analysis sequence needs to be computed. In addition, mutual contamination or cross-talk between different kernels and kernel slices can be eliminated. (for details see my above patent)

OPERATION OF THE INVENTION

Mode 1 of the Invention—Why and How It Works—FIG. 2a

Consider the case where the retina is stimulated pseudo-randomly as taught by the prior art and the first order kernel is computed as schematically illustrated in FIG. 2a. The responses to the preceding and following stimulus are added and subtracted approximately the same number of times. One might thus conclude that the stimulus presented in the following stimulus interval does not contribute to the first order kernel associated with each stimulus patch. However, this is only correct if a response generated by the pseudo-random stimulus does not affect the responses to the following stimuli. By definition, the first order response contains all features of the signal that correlate with the pseudorandom stimulation, including its effects on the stimulus in the following stimulus interval.

Figure 5A:
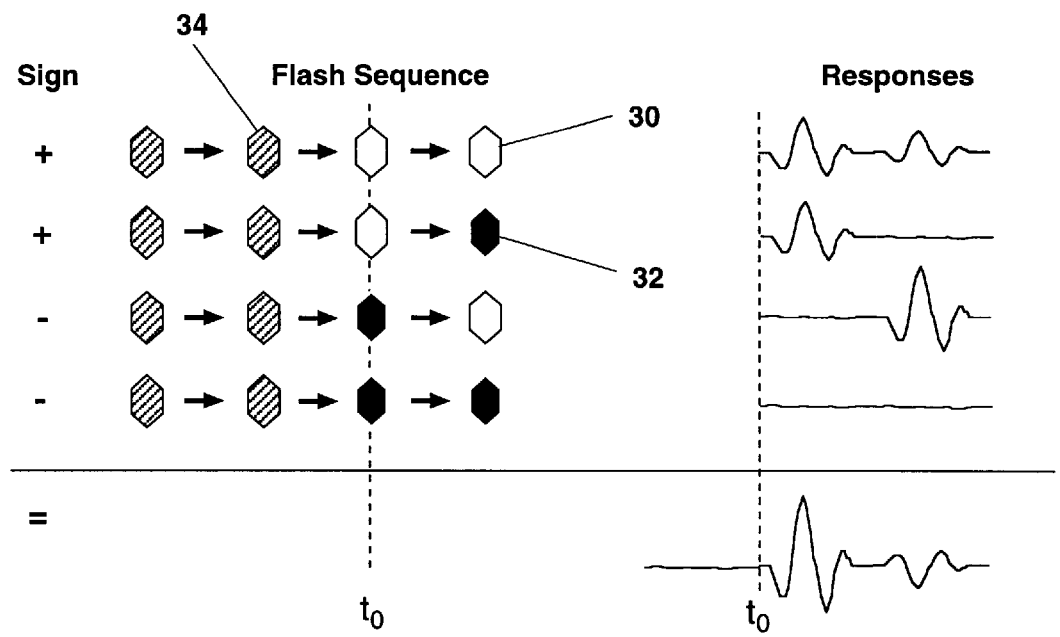
FIG. 5a is a schematic representation of the derivation of the first order binary kernel for comparison with FIG. 6a and 6b.
Figure 5B:
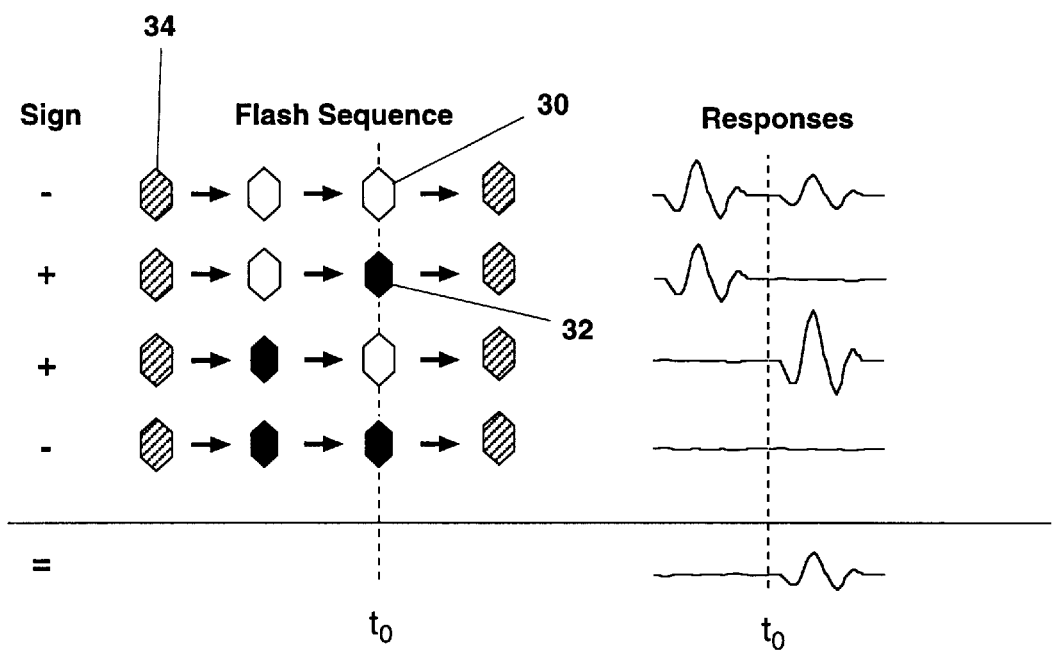

FIGS. 5a and 5b—Second Order Effects on the Kernels: Local Contributions

FIG. 5a graphically illustrates the derivation of the first order kernel, taking into consideration effects of the pseudorandom stimulus on the response to the following stimulus. In this example each stimulus is assumed to reduce the response in the following stimulus interval. By comparing the derivation of FIG. 5a with that of the first slice of the second order kernel shown in FIG. 5b, one can easily verify that the contribution to the first order kernel from the following stimulus interval is identical with the inverted second order kernel slice. Both of these response components are second order effects of the binary stimulus. In the case of multi-area stimulation, the two second order effects are only identical (except for polarity) if the stimulation of a stimulus patch does not affect the responses generated at other patches. This case will be considered below.

As the second order contributions to the first and second order kernels are identical in waveform and amplitude except for the polarity, the signal-to-noise ratio can be enhanced by adding the two with the proper relative shift and sign. To this end the second order first slice is advanced by one stimulus interval and subtracted from the first order kernel. This operation does not affect the contributions from the stimulus sequences in the first and the third line in FIG. 5a and FIG. 5b. Both contributions are identical in the two figures in signal and noise. However, it cancels the contributions from the stimulus sequences of the second and the fourth lines which contain only noise. The operation thus eliminates half of the additive noise contamination and enhances the signal-to-noise ratio in the second order effect by a factor of $\sqrt{2}$.

Figure 6A:
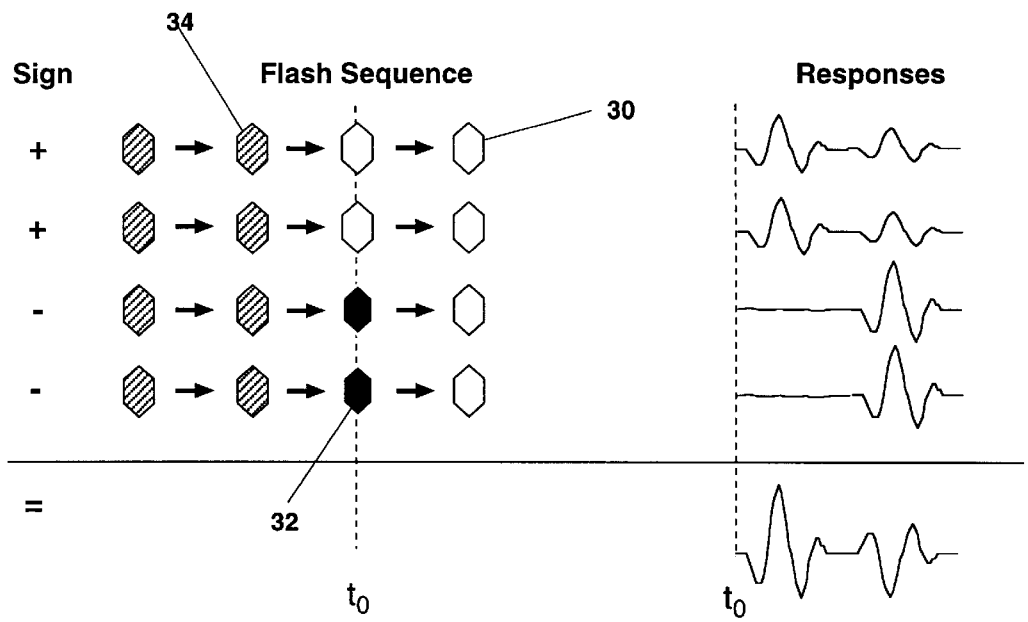
FIG. 6a is a schematic representation of the derivation of the first order binary kernel for Mode 1 of the invention.
Figure 6B:
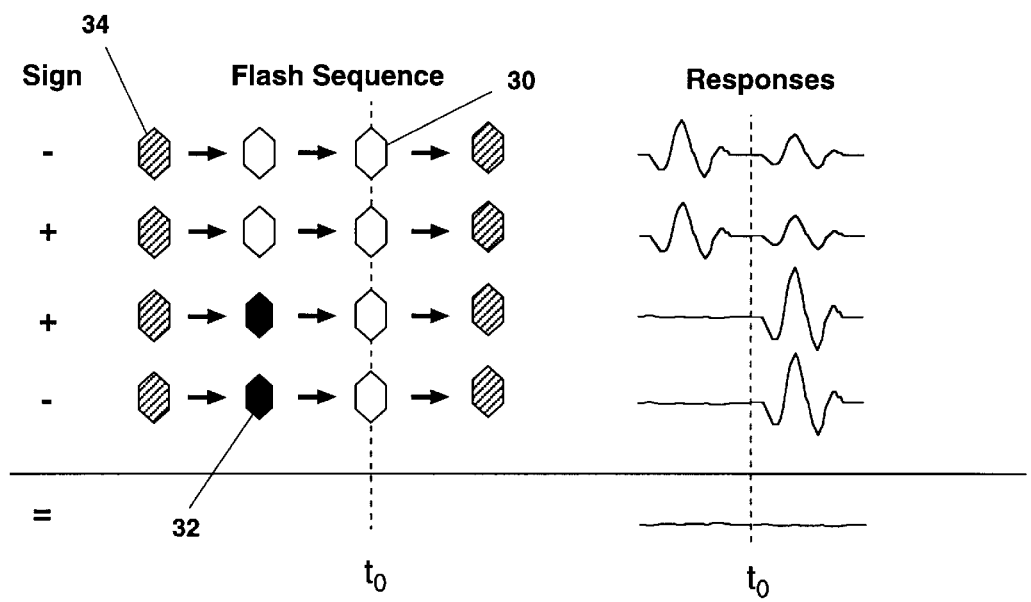
FIG. 6b is a schematic representation of the computation of FIG. 5b for the case where a periodic stimulus is applied at the same stimulus patch after every pseudorandom stimulus.

FIG. 6a and 6b—Enhancing the Second Order Effects through Mode 1: Local Contributions In mode 1 each stimulus following a pseudorandom stimulus is a periodic stimulus occurring each time as shown in FIG. 6a. This modification leads to a doubling of the response amplitude while having no effect on the noise which is assumed to be additive. Stimulation mode 1 thus leads to an improvement in the signal-to-noise ratio of the second order effect in the first order kernel by a factor of 2 while eliminating the corresponding first slice of the corresponding second order kernel as shown in FIG. 6b.

Figure 7A:
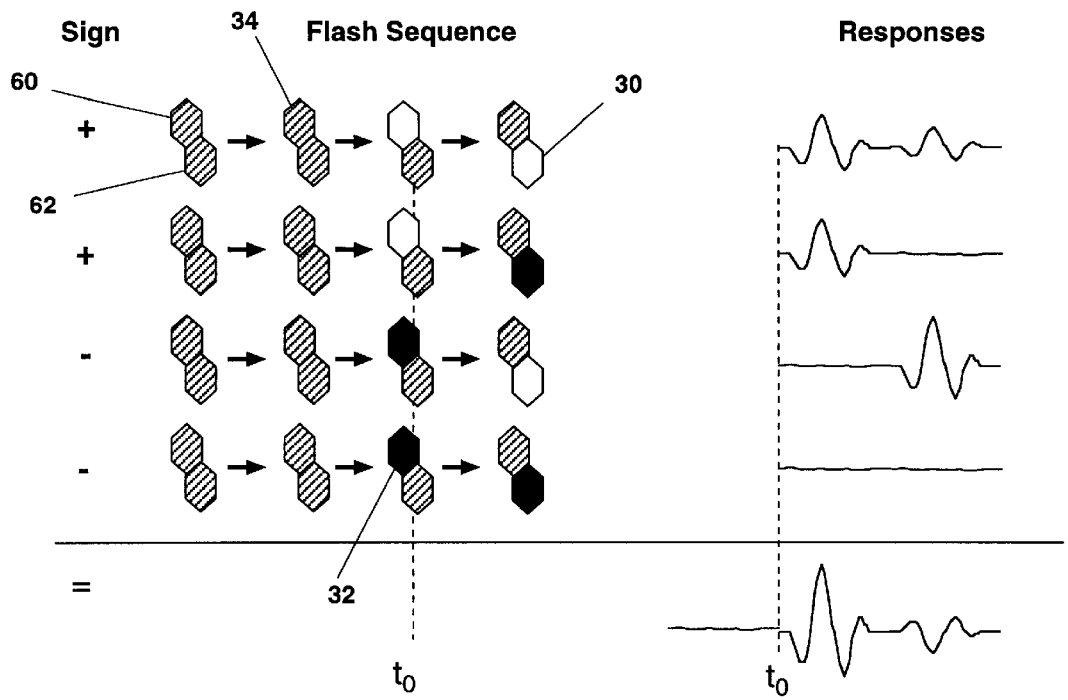
FIG. 7a is a schematic representation of the derivation of the first order binary kernel showing the second order contribution from a different stimulus patch for for comparison with FIGS. 8a and 8b.
Figure 7B:
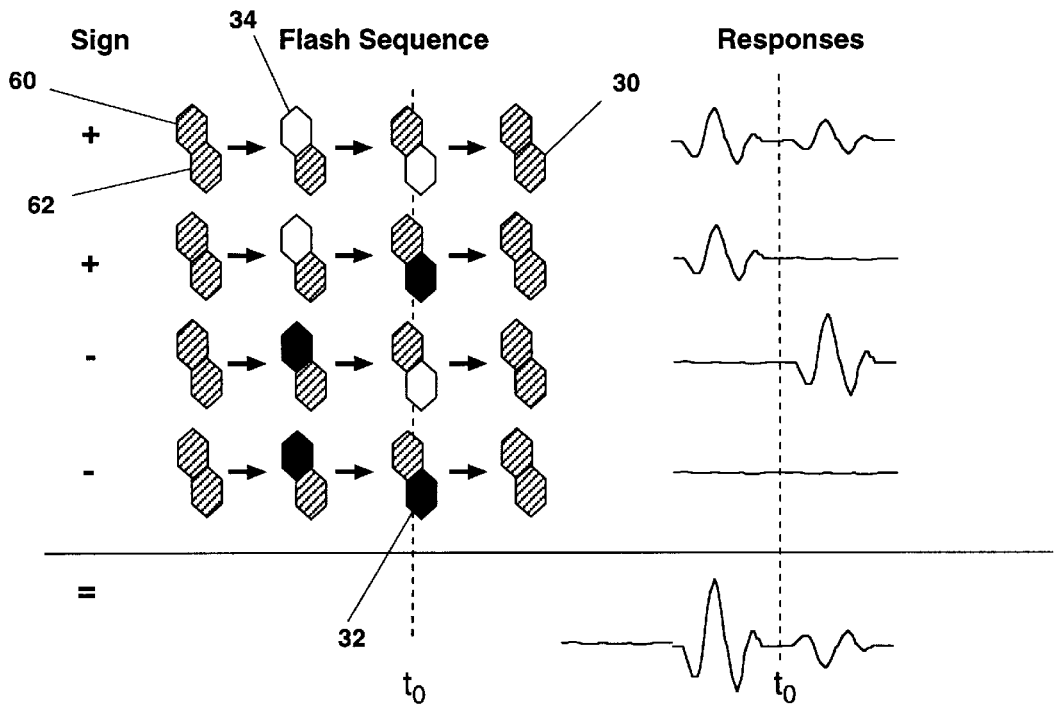
FIG. 7b is a schematic representation of the derivation of the first slice of the second order binary kernel for for comparison with FIGS. 8a and 8b.

FIGS. 7a and 7b—Second order Effects on the Kernels: Local Contributions

FIG. 7a illustrates the interaction between two stimulus patches 60 and 62 patch 1 and patch 2 respectively. Specifically the figure illustrates the effect of a stimulus on patch 1 on the response to a stimulus at patch 2 in the following stimulus interval. In this example only the contributions to the first order response of patch 1 from one neighboring patch 2 are considered. All other second order effects such as the interaction between stimuli at the same patch and at patches other than patch 2 that would also contribute to the first order kernel are assumed to be zero. The bottom panel shows the derivation of the second order mutual kernel slice between patch 1 and patch 2 for a relative lag between the stimuli of one stimulus interval. Again, we see that the contribution to the first order kernel from the response to a stimulus in the following stimulus interval at patch 2 is identical with the inverted second order kernel shown in FIG. 7b.

Figure 8A:
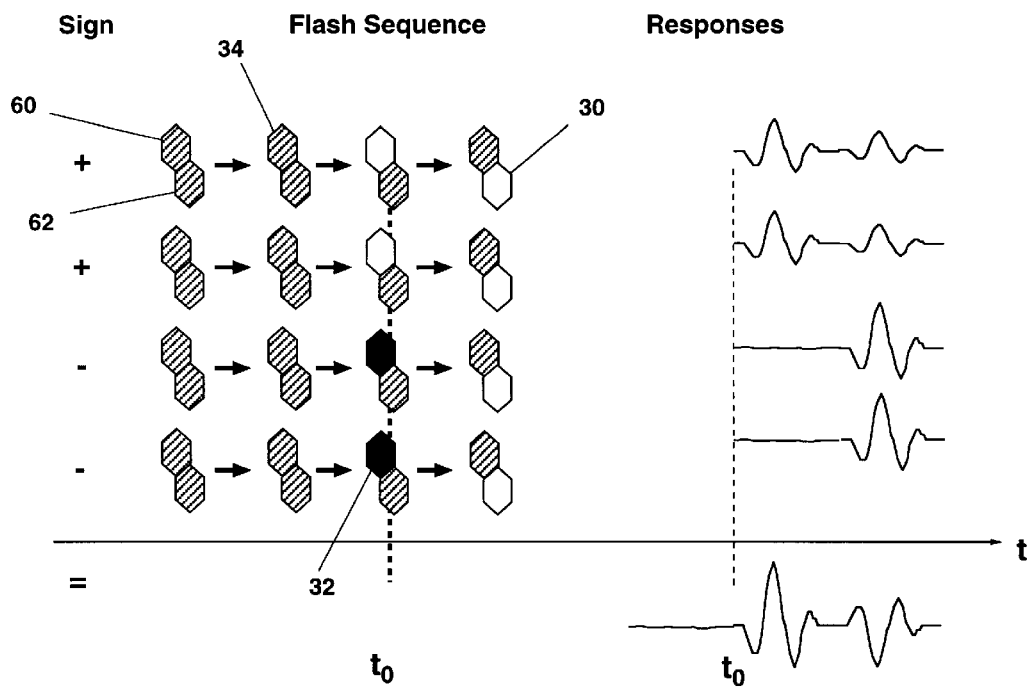
FIG. 8a is a schematic representation of the derivation of the first order binary kernel for the case where a periodic stimulus is applied at a different stimulus patch after every pseudorandom stimulus according to Mode 1 of the invention.
Figure 8B:
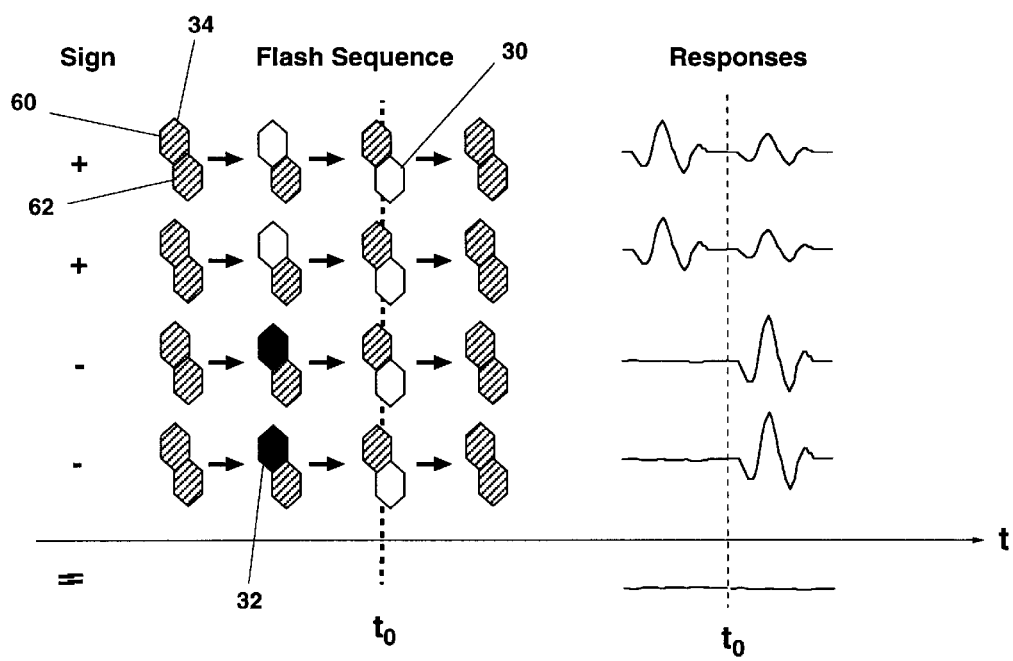
FIG. 8b is a schematic representation of the of the computation of FIG. 5b for the case where a periodic stimulus is applied at a different stimulus patch after every pseudorandom stimulus according to Mode 1 of the invention.

FIG. 8a and 8b—Enhancing the Second Order Effects through Mode 1: Lateral Contributions Consider now stimulation mode 1 wherein each stimulus following a pseudorandom stimulus is a periodic stimulus occurring in each time interval at all stimulus patches FIG. 8a. This modification leads to a doubling of the response amplitude while having no effect on the noise. Stimulation mode 1 of the invention thus leads to an improvement in the signal-to-noise ratio of this component by a factor of 2. Mode 1 thus leads to an improvement in the signal-to-noise ratio of the second order effect in the first order kernel by a factor of 2 while eliminating the corresponding first slice of the corresponding second order kernel as shown in FIG. 8b.

FIGS. 7a, 7b, 8a and 8b were drawn with the assumption that only the contributions to the first order response from one neighboring patch 2 are different from zero. However, in general the first order kernel receives second order contributions from the same patch as well as from all patches in the surrounding area. While each individual contribution may be small, together they add up to a considerable signal. Extracting all these contributions from a record obtained with conventional pseudorandom multi-areal stimulation is usually not feasible, since the record length necessary to encode and separate so many response components would be much too long for a single recording session in a clinic. Furthermore the improvement in the signal to noise ratio would only be $\sqrt{2}$ times the sum of the second order mutual kernel slices. Mode 1 has the effect of automatically adding all the contributions to the first order kernel. It does not require lengthening of the recording and improves the signal-to-noise ratio by a factor of 2 rather than $\sqrt{2}$.

Application 1: In its early stages glaucoma is thought to affect only retinal ganglion cells, leaving the conventional first order multi-area response largely unaffected. Mode 2 amplifies those components of the multi-area response that receives a larger contribution from retinal ganglion cells. Mode 1 is therefore a means for diagnosis and management of glaucoma.

Application 2: Consider the case where the pseudorandom stimulus in each stimulus interval stimulates the retinal rods while a large area white flash stimulus presented in all intervals stimulates the cones. The direct multi-area response due to rod stimulation is very small and difficult to evaluate. However, their stimulation has a strong effect on the following cone mediated response to the large area flash in the same location as well as in the surrounding area. Through this effect the function of retinal rods can be measured at in each stimulus area and mapped across the retina.

Figures 4A, 4B:
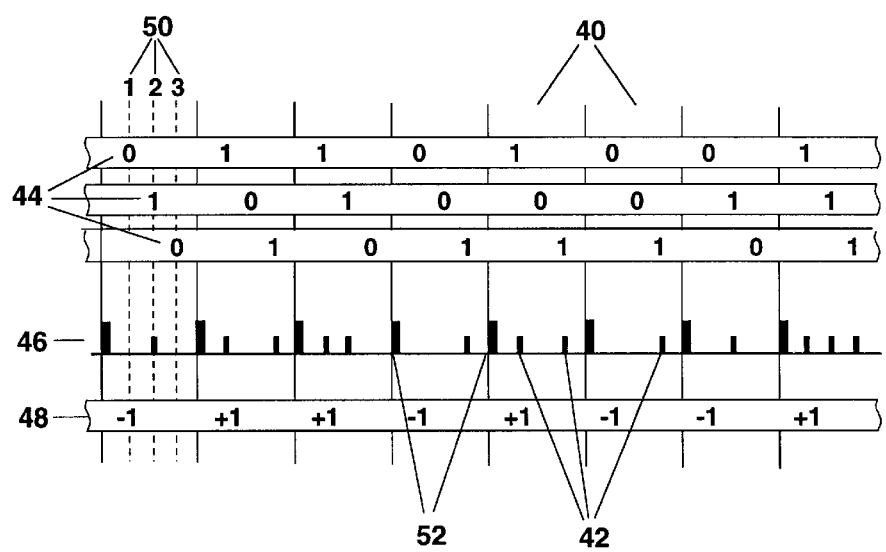
FIG. 4a symbolizes an m-sequence (top) and a sequence derived from it controlling the stimulation of mode 2 (bottom) used in mode 2 of the invention.
FIG. 4b is a schematic representation of stimulus and analysis sequences derived from the sequences of FIG. 4a. used in Mode 2 of the invention.

Mode 2—FIGS. 4a and 4b

In this mode the stimulation at a predetermined number k of time points 50 within each stimulus interval is controlled by the same pseudorandom sequence. The responses generated by stimuli at each of time points 50 thus correlate with analysis sequence 48. Since the stimulation sequence is shifted from one time point to the next by L/k steps, the responses corresponding to the different time points 50 are found on the cross-correlation cycle shifted relative to one another by L/k steps.

Application 1: If points 50 of stimulation in each stimulus interval are equally spaced and if the stimuli presented pseudorandomly at all time points are identical, this method provides multiple independent estimates of the first order kernel. These estimates can be used to compute the mean and standard deviation along the response waveforms.

Application 2: When the stimuli presented at different time points within the stimulus interval are of a different nature (different luminance, color, geometry, duration, etc.) method 2 permits the simultaneous derivation of the corresponding responses from a single record.

Application 3: A stimulus is applied periodically at the beginning of each stimulus interval. The response is derived separately at each of selected time points 50 in stimulus interval 40. If the periodic stimulus is a bright flash, the responses derived by method 2 at time points 50 reflect the recovery of the response from the effects of the bright flash. If the periodic stimulus selectively stimulates the retinal rods and the stimuli at the different time points selectively stimulates the retinal cones, then the results from method 2 reflect the time course of the effect of rod stimulation on the cone mediated responses.

Simplified Flow Chart for Data Collection and Processing—FIG. 9

The preferred implementation utilizes stimulation with binary m-sequences as taught in my above Patent and my U.S. Pat. No. 5,667,577 of Sep. 16, 1997. A simplified flow chart for such an implementation is shown in FIG. 9. The same flow chart applies to both Modes as well as their combined application. The modes differ in the number of stimulus updates during a stimulus interval and in the type of stimuli generated. Further details concerning the use of the m-sequence technique for the implementation of the invention are found in my above patents.

In preparation for the actual data collection the following steps are executed:

70—The stimulus geometry is drawn on the stimulus screen. It consists of an array of stimulus areas. Each stimulus area can assume two states that differ in color, luminance and/or pattern.

72—A stimulus table is set up to specify the video frame within each stimulus interval where the display is updated to the corresponding stimulus.

74—Data collection timers are set up to initiate analog-to-digital conversion of a specified number of data points per video frame.

76—A frame counter is initialized to count the video frames in each stimulus interval.

78—A sample counter is initialized to count the samples in each video frames.

80—An interval counter is initialized to count the $2^n-1$ stimulus intervals in the stimulus sequence.

82—A table is set up to contain all $2^m-1$ elements of the m-sequence used for stimulation.

Data are collected using the nested loops shown on the right in FIG. 9:

Loop 84 contains the collection of data during the entire stimulation cycle comprising n32 $2^m-1$ stimulus intervals.

Loop 86 contains the collection of data during a stimulus interval.

Loop 88 updates the stimulus in accordance with the stimulus table. When the frame count matches an entry in the stimulus table, the corresponding stimulus is loaded on retrace of the video scan.

Loop 90 collects a specified number of data points during each video frame.

92—The cross-correlation function between the response sequence and analysis sequence 48 is computed.

94—The response components corresponding to the stimulus areasare extracted. First order responses to m-sequence controlled stimuli at the same time point within the stimulus interval are found on the cross-correlation cycle separated by (n*r)/(k*l) data points where k is the number of m-sequence modulated stimuli in each stimulus interval, l is the number of stimulus areas and r is the total number of data points collected in a stimulus interval. Responses of the same stimulus area but to m-sequence controlled stimuli at the different time point within the stimulus interval are found separated by st+(n*r)/k, where st is the corresponding offset from the stimulus table.

The above steps are implemented in computer 14 by a suitable program, preferably in the C++ language.

Conclusion, Ramifications and Scope of the Invention

The reader will thus see that the methods of the invention produces highly advantageous and unexpected results. The modification of Mode 1 greatly enhances response components of the multi-area electroretinogram that response components that are known to be important for the diagnosis of diseases affecting retinal function. By increasing the signal-to-noise ratio in these components it permits shortening of the recording times in the clinic while increasing the sensitivity of the technique for the detection of retinal dysfunction. Mode 2 permits the user to follow the time course of adaptive processes in the retinal and determine their rate of change. Such processes, in particular the recovery of function after bright flashes, are known to be affected in retinal diseases. They are commonly tested by psychophysical means, i.e., with tests requiring the response of the patient. With Mode 2 it is now possible to measure these retinal properties objectively and simultaneously at a large number of retinal areas. With Modes 1 and 2 it is now possible to concurrently stimulate the retina with different stimuli and measure the interaction between these stimuli on a time scale of milliseconds. Of particular interest is the interaction between responses due to selective stimulation of retinal rods and cones. The new modes of multi-area ERG analysis opens up a range of clinical applications that are yet to be explored.

While the foregoing description contains specific methods, hardware, and parameters, many variations and ramifications within the scope will be envisioned by those skilled in the art. For example, the method of obtaining signals evoked by visual stimulation can be varied, e.g., using EEG signals or pupillary responses. The modulation of the areas of the stimulus array can be adjusted and the shapes of the areas can be varied and optimized for the problem at hand. The programming steps can be varied, specifically the method for performing the cross-correlation. If the stimulus sequence is derived from a binary m-sequence, all kernels can be derived by means of a single cross-correlation between the response and the m-sequence and the cross-correlation can be performed by means of a the fast M-Transform as taught by my above patents.

Also the range of applications of the methods of the invention both in medical research and clinic is large. E.g., it can be used to study pathological changes in range and dynamics of interactions in the retina and along the visual pathway. It can be used locallized such changes int the visual field and to map their spatial extent.

Accordingly, the scope of the invention should not be determined by the specific implementations and uses illustrated, but by the appended claims and their legal equivalents.

I claim:

1. A method of deriving response properties of a system with a plurality of inputs using a stimulus sequence comprising:

providing each input with a stimulus sequence having a plurality of intervals of equal length, corresponding to elements in a pseudorandom sequence with values 0 and 1, said sequence having pseudorandom stimuli of a first type at the beginning of said intervals if the corresponding element of said pseudorandom sequence is a 1, said sequence containing a stimulus of a second type at a predetermined time within each of said intervals said inputs having equally distributed starting points said stimulus sequence.

2. The method of claim 1 further including computing the cross-correlation cycle between a response cycle obtained through stimulation with said stimulus sequence and an analysis sequence derived from said pseudorandom sequence, said analysis sequence comprising the same number of elements as said response cycle, elements with the values +1 at locations where the first of said inputs is stimulated in accordance with a 0 in said pseudorandom sequence and a−1 where the first of said inputs is stimulated in accordance with a 1 in said pseudorandom sequence, all other elements of said analysis sequence having the value 0, extracting said effects of stimulation of said inputs from consecutive locations on said cross-correlation cycle, starting at locations corresponding to said starting points of said inputs in said stimulation cycle.

3. The method of claim 1 wherein said pseudorandom binary sequence is a binary m-sequence.

4. A method of stimulation comprising:

providing a stimulus sequence controlled by k consecutive cycles of a binary m-sequence of length $2^n-1$ where n is a positive integer and k is a power of 2, said stimulus sequence consisting of $2^n-1$ stimulus intervals each controlled by k consecutive elements of said binary m-sequence said consecutive elements controlling k consecutive subdivisions of said stimulus intervals.

5. The method of claim 4 wherein each of said stimulus intervals contains a plurality of additional stimuli that are not dependent of said binary m-sequence.

6. A method of deriving from a response sequence to a stimulus sequence having stimulus intervals the response components corresponding to k subdivisions of said stimulus intervals, comprising:

computing the cross-correlation sequence between the response sequence obtained through stimulation with said stimulus sequence and an analysis sequence derived from a binary m-sequence, said analysis sequence being subdivided into $2^n-1$ analysis sequence segments corresponding to said $2^n-1$ stimulus intervals, said analysis sequence segments containing k consecutive analysis interval elements, the first of said analysis interval elements having the value +1 if the first element of said m-sequence contained in said stimulus interval corresponding to said analysis interval has the value 0 and a −1 if the first element of said m-sequence contained in said stimulus interval corresponding to said analysis interval is a 0, all other elements having the value 0.

finding the starting points of said responses corresponding to the said k subdivisions on said cross-correlation sequence at intervals measuring $2^n/k$ of said analysis intervals, and extracting said responses corresponding to the said k subdivisions from said cross-correlation sequence.

7. The method of claims 6 wherein a predetermined number 1 of inputs are concurrently stimulated comprising:

stimulating of said inputs with the same said stimulus sequence while the starting point in said stimulus sequence is shifted along said stimulus sequence from one of said inputs to the next a number of said stimulus intervals equal to $2^n/(k*l)$.

8. The method of claim 6 further including:

computing the cross-correlation sequence, finding on said cross-correlation sequence the starting points of said responses corresponding to said k subdivisions of said stimulus intervals, all starting points being spaced at intervals measuring $2^n/(k*l)$ in units of said analysis intervals, grouping said starting points in k groups of l consecutive members whereby said k groups correspond to said responses corresponding to the said k subdivisions and said l members correspond to said l inputs, extracting said time slice responses from said cross-correlation sequence for said l inputs.

9. The method of claims 8 wherein said predetermined number of inputs is a power of 2.

* * * * *